United States Patent [19]

Göring et al.

[11] Patent Number: 5,213,799
[45] Date of Patent: May 25, 1993

[54] TWO-PHASE COSMETIC COMPOSITION

[75] Inventors: Stefan M. Göring, Niedernhausen; Claudia Koss, Alsbach, both of Fed. Rep. of Germany

[73] Assignee: Goldwell AG, Darmstadt, Fed. Rep. of Germany

[21] Appl. No.: 802,549

[22] Filed: Dec. 5, 1991

[30] Foreign Application Priority Data

Jan. 10, 1991 [DE] Fed. Rep. of Germany ....... 4100490

[51] Int. Cl.$^5$ .......................... A61K 7/02; A61K 7/48
[52] U.S. Cl. .................... 424/401; 514/844; 514/845; 514/846; 514/847; 514/848; 514/938; 514/943
[58] Field of Search ............... 424/401, 78.03; 514/845, 846, 847, 848, 938, 943

[56] References Cited

U.S. PATENT DOCUMENTS

| | | | |
|---|---|---|---|
| 4,035,513 | 7/1977 | Kumano | 424/177 |
| 4,451,493 | 5/1984 | Miller et al. | 426/602 |
| 4,454,113 | 6/1984 | Hemker | 424/63 |
| 4,661,343 | 4/1987 | Zabotto et al. | 514/845 |

FOREIGN PATENT DOCUMENTS 3627313 2/1988 Fed. Rep. of Germany.

OTHER PUBLICATIONS

Patent Abstracts of Japan vol. 12, No. 155 (C-494) (3002) 12 May 1988.
English Abstract of German Patent No. 36 27 313.

*Primary Examiner*—Thurman K. Page
*Assistant Examiner*—Carlos Azpuru
*Attorney, Agent, or Firm*—Birch, Stewart, Kolasch & Birch

[57] ABSTRACT

This invention refers to cosmetic compositions, particularly a skin treating preparation, comprising a transparent oil phase and a transparent aqueous phase, preferably with humectant effect, which permits a homogeneous mixture when being shaken, and which separates again in two transparent phases thereafter. These properties are achieved by the addition of 0.1 to 1.0% by weight of a $C_{12}$–$C_{18}$ fatty acid triglycerol ester.

5 Claims, No Drawings

TWO-PHASE COSMETIC COMPOSITION

This invention relates to a liquid cosmetic composition consisting of two separate phases, especially a skin or hair care preparation.

Two-phase skin care preparations, especially emulsions, are known per se, see for example DE-PS 3 627 313. These products are either available in an opaque form and/or are mixed by shaking before application onto the skin. If one or both phases are of transparent nature, they quickly separate again after shaking or application onto the skin so that the product cannot penetrate into the skin, or the phases remain permanently mixed in an opaque emulsion after application.

The present invention starts from the problem of developing a cosmetic composition, particularly a skin care preparation, having two separate transparent phases which, when mixed and shaken, for a certain time form a homogeneous phase by partial emulsification, that may be applied homogeneously onto the skin, and that separates again into two different transparent phases afterwards.

The solution of this problem is the addition of a small quantity of a $C_{12}$–$C_{18}$ fatty acid monoester of triglycerol to a cosmetic composition, particularly a skin treatment preparation consisting of a transparent fat and oil phase and of a transparent aqueous phase, preferably containing one or more humectant substances.

It was surprising and not foreseeable that, just by the use of these substances, a homogeneous but non-stable emulsion can be achieved by mixing the originally separate oil and water phases which completely disintegrate again after a short period of time (approx. 5 to 10 minutes).

Particularly triglycerol monolaurate, triglycerol monostearate or isostearate, triglycerol monooleate or also fatty acid mixtures such as triglycerol monococoate, used in a proportion of 0.1 to 1%, especially 0.2 to 0.5 by weight, have proved to be suitable $C_{12}$–$C_{18}$ fatty acid monoesters of triglycerol.

A particularly preferred monoester of triglycerol is triglycerol monolaurate (Polyglyceryl-3-laurate),

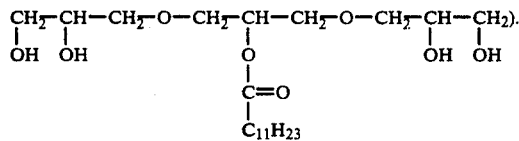

The fat and oil phases, whose proportion in the total skin treatment composition is 20 to 40% by weight, preferably approximately 25% by weight, may comprise those fats and oils usually applicable in skin care preparations.

As such are mentioned: squalene and its synthetic substitutes, vegetable oils such as olive, avocado, jojoba, sesame, wheat germ, soybean, peanut, almond oils and also paraffin oil, fatty acid esters such as decyl oleate, isopropyl myristate or ethyl isostearate, fatty alcohols such as dodecanol, fatty acid diglycerides and triglycerides, silicones, etc.

The aqueous phase of the skin treatment composition may contain one or more skin humectants besides the triglycerol monofatty acid esters, as defined above.

These are well-known to the expert, e.g., urea, amino carboxylic acids and their mixtures and compounds, e.g., the so-called "NMF" (natural moisturizing factor), protein hydrolyzates, pyrrolidone carboxylates, sugar-amino acid condensates and also special plant extracts.

Humectants are usually added in a proportion of 1 to 5% preferably 2 to 4% by weight, with reference to the total skin treatment composition.

The skin care preparations of this invention may comprise all of the usual agents and auxiliary substances which are, depending on their solubility, added either to the oil or fat phase or to the aqueous phase.

Those substances familiar to an expert include, e.g., water-soluble and fat-soluble vitamins, plant extracts, ultraviolet absorbers, dyestuffs, blood circulation stimulating agents, preservatives, solvents and diluents such as glycerol and diols, buffer substances, refattening substances, surface-active substances, perfume oils, and the like.

The pH value of skin treatment compositions of the invention is preferably set within the slightly acidic range of between 5 and 7.

The following is an example of the composition of a skin care preparation in accordance with this invention:

| 1. Oil phase: | |
| --- | --- |
| Squalene | 14.00% by weight |
| Silicone oil | 2.00 |
| Fatty alcohol | 3.00 |
| Fatty acid triglyceride | 4.00 |
| Jojoba oil | 2.00 |
| Blue dyestuff | 0.005 |
| UV absorber | 0.01 |
| 2. Aqueous phase | |
| Urea | 0.75% by weight |
| Amino acid mixture | 0.60 |
| Plant extract | 1.00 |
| Glycerol | 4.00 |
| 1,3-Propandiol | 3.50 |
| Preservative agents | 0.30 |
| Triglycerol monolaurate | 0.30 |
| Buffer (sodium phosphate/citric acid) | 0.35 |
| Water | ad 100.00 |

When filled into transparent bottles, the composition develops two separate, clear phases.

Upon shaking, these phases mix to become homogeneous, and they disintegrate again after a standing period of approximately 8 to 10 minutes.

A substitution of the triglycerol monolaurate by the same quantity of
  a) polyethylene glycol-7-glyceryl cocoate,
  b) polyethylene glycol-40 hydrogenated castor oil,
  c) polyethylene glycol-60 hydrogenated castor oil,
  d) polysorbate 80
  e) polyethylene glycol-9 tridecylether,
  f) polyethylene glycol-5 octanoate, and
  g) polyethylene glycol-5 lauryl ethoxylate-7,
which are well-known standard emulsifiers or solubilifers, did not lead to phases that are homogeneously miscible, nor to those which disintegrate again into clear phases after having been mixed.

A liquid hair treatment composition according to the present invention was also prepared comprising two separate phases:

| Phase 1: | |
| --- | --- |
| Silicone oil | 24.2% (by weight) |
| Jojoba oil | 0.4% |
| Phase 2: | |

-continued

| | |
|---|---|
| Triglycerol monolaurate | 0.1–0.5% (by weight) |
| 0,2M Citric acid (in water) | 3.9% |
| 1M Sodium chloride (in water) | 4.0% |
| Water | ad 100.00% |

What is claimed is:

1. A two-phase cosmetic composition comprising two separate transparent phases that form a homogeneous phase when mixed by shaking, wherein said homogeneous phase separates thereafter into said two separate transparent phases, wherein one of said transparent phases is a fat or oil phase and the other of said transparent phases is an aqueous phase, and wherein said composition contains 0.1 to 1.0% by weight, calculated to the total composition, of a $C_{12}$–$C_{18}$ fatty acid monoester of triglycerol.

2. The cosmetic composition according to claim 1, containing 0.1 to 1.0% by weight of the total composition of a fatty acid monoester of triglycerol selected from the group consisting of triglycerol monlaurate, triglycerol monococoate, triglycerol monostearate, triglycerol isostearate and triglycerol monooleate.

3. The cosmetic composition according to claim 2, containing 0.2 to 0.5% by weight of the total composition of triglyercol monolaurate.

4. A skin treatment composition according to claim 1, comprising 20 to 40% by weight of a transparent fat or oil phase and 50 to 60% by weight of a transparent, humectant-containing aqueous phase.

5. A skin treatment composition according to claim 4, wherein said composition has a pH value between 5 and 7.

* * * * *